United States Patent

Robba et al.

[11] 4,186,136
[45] Jan. 29, 1980

[54] NOVEL BENZOTHIENYL AMINO (PROPYL AND BUTYL) KETONES, A METHOD OF PREPARATION THEREOF AND THEIR APPLICATION TO THERAPEUTICS

[75] Inventors: Max F. Robba; Michel Aurousseau, both of Paris, France

[73] Assignee: Innothera, Arcueil, France

[21] Appl. No.: 672,109

[22] Filed: Mar. 31, 1976

[30] Foreign Application Priority Data

Apr. 3, 1975 [FR] France .................. 75 10422

[51] Int. Cl.² .................. C07O 333/52; C07O 207/12; A01N 9/00; A01N 9/22
[52] U.S. Cl. .................. 544/146; 260/326.5 SA; 544/69; 544/131; 546/202; 424/275; 424/248.51; 424/267; 424/274; 546/194; 546/274; 546/13; 260/330.3; 260/244.4
[58] Field of Search .................. 260/330.5, 326.5 SA; 544/146; 546/202

[56] References Cited

U.S. PATENT DOCUMENTS 3,417,087 12/1968 Campaigne et al. .............. 260/330.5

Primary Examiner—A. Siegel
Attorney, Agent, or Firm—Blanchard, Flynn, Thiel, Boutell & Tanis

[57] ABSTRACT

Compounds having the formula

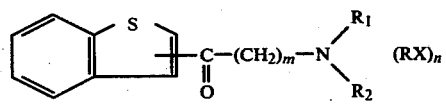

wherein $R_1$ and $R_2$ are alkyl having one to 4 carbon atoms, allyl or

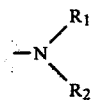

is pyrrolidino, piperidino, perhydroazepino or morpholino, RX is an inorganic acid, organic acid or an alkyl bromide or iodide, m is 3 or 4, and n is zero or one. The compounds are prepared by (1) reacting benzothienyl-lithium with

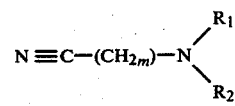

followed by hydrolysis, or (2) when the substituent is located at the 2 position of the benzothienyl group, by reacting benzothiophene with

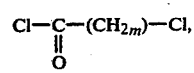

followed by reaction with

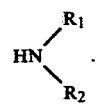

The compounds possess blood-plaque aggregation, spasmolytic, analgesic, anti-inflammatory and coronary, cerebral and peripheral vaso-dilatory properties.

11 Claims, No Drawings

NOVEL BENZOTHIENYL AMINO (PROPYL AND BUTYL) KETONES, A METHOD OF PREPARATION THEREOF AND THEIR APPLICATION TO THERAPEUTICS

The present invention has at its object novel benzothienyl amino (propyl and butyl) ketones, a method of preparation thereof and their application in therapeutics.

The compounds of the invention have the general formula:

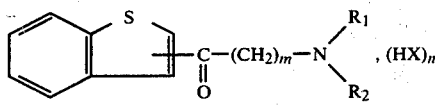

where:
$R_1$ and $R_2$ designate each an alkyl radical saturated or not having 1 to 4 carbon atoms to form together with the nitrogen atom to which they are bound a heterocyclic radical chosen from the following: pyrrolidino, piperidino, perhydroazepino and morpholino; and HX represents an acid compound chosen from the following:
- hydrochloric acid, bromhydric acid, sulphuric acid, phosphoric acid, boric acid;
- oxalic, maleic, malic, fumaric, citric, embonic, methane sulfonic, acetylsalicylic, nicotinic, parachlorophenoxyacetic or parachlorophenoxyisobutyric acid;
- methyl bromide, methyl iodide, ethyl bromide, butyl bromide, benzyl bromide;

m is worth 3 or 4; and
n represents 0 or 1.

The method of the invention comprises the following succession of operations:
reaction of bromobenzothiophene of formula (II)

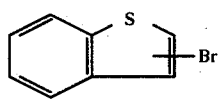

on n.butyl-lithium of formula (III):

to give benzothienyl-lithium of formula (IV)

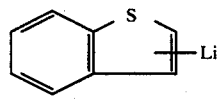

addition of an aminoalkylnitrile of formula (V)

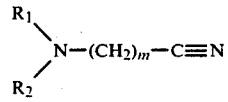

where $R_1$, $R_2$ and m have the same significance as in formula (I) on the benzothienyl-lithium previously obtained to produce a compound of formula (VI)

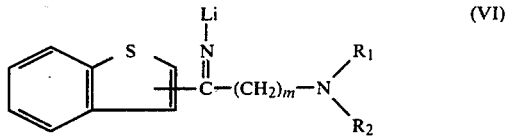

which is hydrolised to finish up directly with the ketone of formula (I)

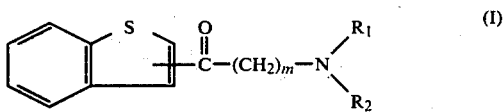

which may be subjected to a
salification by an acid compound of formula HX defined above, which gives salts of formula

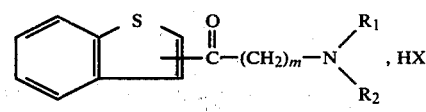

It is also possible to prepare compounds of formula (I'):

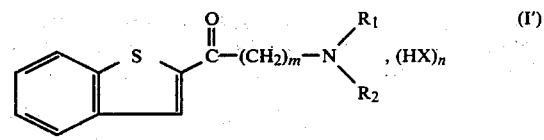

where $R_1$, $R_2$, HX, m and n have the same significance as above, by the following succession of operations:
condensation of a chlorated acid chloride of formula (VII)

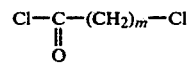

where m is worth 3 or 4,
on benzothiophene of formula (VIII):

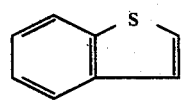

in the presence of a Lewis acid, from which results the chlorated ketone of formula (IX):

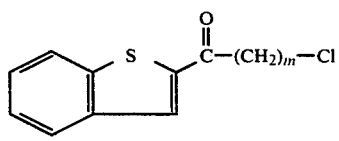

followed by a
condensation of amine of formula (X)

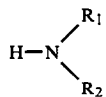

where:
R₁ and R₂ have the same value as in formula (I) on said compound of formula (IX)
to give the basis of formula (I)

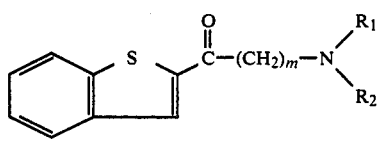

which may be subjected to
salification by an acid compound of formula HX such as defined above.

The following preparations are given as examples.

EXAMPLE 1: 1-(benzothien-2'-yl)-4-N-morpholino butanone

A solution of n-butyl lithium in 100 ml of anhydrous diethylic ether is prepared at 0° C. from 14 g of lithium and 14 g of n-butyl bromide. A solution of 13 g of 2-bromo benzothiophene in 50 ml of diethylic ether is slowly added with agitation, under nitrogen and at a temperature of −20° C. Agitation continues for two hours. 15 g of 4-N-morpholino butyronitrile is poured in. Agitation is carried out for 16 hours at −20° C. Hydrolysis is carried out by pouring with agitation on to 150 g of piled ice. The ether is decanted and the aqueous phase extracted with ether. The united etherated phases are dried on disodic sulfate and the solvent is evaporated. The residue is recrystallized in cyclohexane.

Thus is obtained, with a yield of 60%, white crystals having a melting point of 61° C.

EXAMPLE 2: 1-(benzothien-2'-yl)-4-N-morpholino butanone hydrochloride

Compound 1 in basic form is transformed into hydrochloride by saturation with a flow of gaseous hydrochloric acid of its solution in ethylic ether.

The resulting product is in the form of white crystals having a melting point of 172° C.

EXAMPLE 3: 1-(benzothien-2'-yl)-4-N,N-diallylamino butanone oxalate

A mixture of 4.6 g of 1-(benzothien-2'-yl)-4-chloro butanone and 1.8 g of diallylamine is heated at reflux for 10 hours. After cooling, 250 ml of water are added to the reaction product, which is alkalysed by addition of soda and extracted with diethylic ether. The ether is dried on disodic sulfate and evaporated. The oily residue is dissolved in the minimum of acetone and heated to reflux for 30 minutes with a solution of 3 equivalents of oxalic acid in acetone. Centrifugation is carried out after cooling and recrystallization in acetonitrile.

Thus are obtained, with a yield of 60%, white crystals having a melting point of 172° C.

The compounds shown in the following tables I and II were prepared in the same way.

TABLE I

| No. of compound | m | −NR₁R₂ | HX | Melting point (°C.) | Recrystallisation solvent | Yield (%) |
|---|---|---|---|---|---|---|
| 4 | 3 | −N(CH₃)₂ | chlorhydric acid | 180 | Acetonitrile | 70 |
| 5 | 3 | −N(piperidino) | chlorhydric acid | 186 | Methanol | 70 |
| 6 | 3 | −N(morpholino) | citric acid | 168 | Acetonitrile (1) + methanol (1) | 50 |
| 7 | 3 | −N(morpholino) | p. chlorophenoxyiso butyric acid | 159 | petroleum ether (1) ethylic ether (4) | 40 |
| 8 | 4 | −N(C₃H₇)₂ | methyl iodide | 142 | Acetonitrile | 40 |

TABLE II

Structure: benzothiophene-C(=O)-(CH$_2$)$_3$-NR$_1$R$_2$, HX

| No. of compound | -N(R$_1$)(R$_2$) | HX | Melting point (°C) | Recrystallisation solvent | Yield (%) |
|---|---|---|---|---|---|
| 9 | -N(C$_2$H$_5$)(C$_2$H$_5$) | bromhydric acid | 138 | absolute ethanol | 65 |
| 10 | -N(C$_2$H$_5$)(C$_2$H$_5$) | p. chlorophenoxy-isobutyric acid | 180 | petroleum ether | 65 |
| 11 | -N(C$_3$H$_7$)(C$_3$H$_7$) | bromhydric acid | 167 | Acetonitrile | 60 |
| 12 | -N(CH(CH$_3$)$_2$)(CH(CH$_3$)$_2$) | bromhydric acid | 165 | Acetonitrile (1) + methanol (3) | 60 |
| 13 | -N(pyrrolidine) | bromhydric acid | 178 | methanol | 70 |
| 14 | -N(piperidine) | bromhydric acid | 227 | methanol | 70 |
| 15 | -N(hexamethyleneimine) | bromhydric acid | 146 | Acetonitrile | 75 |
| 16 | -N(hexamethyleneimine) | citric acid | 162 | Acetonitrile | 75 |
| 17 | -N(morpholine) | bromhydric acid | 186 | Acetonitrile (2) + methanol (1) | 65 |

The compounds of formula (I) were tested on laboratory animals and showed themselves particularly active as blood-plaque aggregation inhibitors. They also showed an appreciable activity as spasmolytic, analgesic, anti-inflammatory agents and coronary, cerebral and peripheral vaso-dilatators.

1. Acute toxicity

The acute toxicity of the compounds of formula (I) were evaluated orally (esophagean probe) on a mouse deprived of food 18 hours before the beginning of the test. The products were placed in suspension in a solution of dilute carboxymethyl cellulose. Calculation of the 50 lethal dose (LD 50) was effected according to the method of Miller and Tainter (Miller L. C., Tainter M. L., Proc. Soc. Exptl. Biol. Med. 1944, 57, 261-264).

The death rate was checked for seven days following the treatment.

Table III gives the 50% lethal doses (LD 50) in milligrammes per kilogramme body weight.

TABLE III

| No. of compound | LD 50 (mg/kg/p.o.) |
|---|---|
| 1 | 1 200 |
| 2 | 1 500 |
| 4 | 950 |
| 5 | 1 300 |
| 9 | >1 200 |
| 10 | 1 100 |
| 11 | 1 100 |
| 12 | 500 |
| 13 | 760 |
| 14 | 850 |
| 15 | 950 |
| 16 | 1 200 |
| 17 | 1 000 |

2. Activity on blood-plaque aggregration

The blood plaques used for these studies were human blood-plaques introduced into the test in the form of blood-plaque rich plasmas (B.P.R.P.).

These latter were obtained as water-repellent material by slow centrifugation from human blood samples.

The study of blood-plaque aggregation was made by means of an aggregate-meter with continuous agitation and graphic recording according to the conventional method. (PROST R. S., SOUVERAIN C. H., DOUMENC J., Etude de l'agrégation plaquettaire à l'aide de l'agrégamètre de MUSTARD-Coagulation, 1971, 4, 2, 145–151).

The agents employed for inducing aggregation were diphosphoric adenosine acid (D.P.A.), 1-(3′,4′-dihydroxyphenyl)-2-methylamino ethanol (adrenaline) and collagene. All these reactants were prepared from mother solutions diluted in a Michaelis' buffer. Their concentration in the test may vary according to the affinity of the blood-plaques.

An optimum concentration is thus sought by successive tests on the same B.P.R.P.

The inhibitory activity on the aggregation was evaluated by addition of the product under study to the B.P.R.P. before introduction of the aggregating agent.

The concentrations of compounds of formula I (X) in the B.P.R.P. are: C (X)=$2.5 \times 10^{-5}$ g/ml for aggregation with D.P.A. and adrenaline, and C (X)=$2 \times 10^{-5}$ g/ml for collagene.

The reference product (R) is 2,6-bis (diethanolamino)-4,8-dipiperidinopyrimido[5,4-d]pyrimidine (known under the trademark "Dipyridamole") used in the concentration C (R)=$5 \times 10^{-4}$ g/ml for aggregation with D.P.A. and adrenaline and C (R)=$2 \times 10^{-4}$ g/ml for aggregation with collagene.

The following table IV indicates the activity of some compounds of formula I: a (X) the activity of the reference product: a (R) and the different values of the ratio:

$$\frac{a(X)}{a(R)}$$

In addition, in order to ensure a better comparison between the activity of the compounds of the invention and that of the reference product, table IV shows the values of the ratio $$\frac{C(X)}{LD\ 50\ (X)} \bigg/ \frac{C(R)}{LD\ 50\ (R)}$$

We get: LD 50 (R)=2150 mg/kg/p.o.)

This table shows that, taking into account the value of the ratio $$\frac{C(X)}{LD\ 50\ (X)} \bigg/ \frac{C(R)}{LD\ 50\ (R)},$$

the inhibitory activity on the blood-plaque aggregation of the compounds of the invention is at least equal to that of the reference product. For certain compounds, such as No. 17, it is even substantially superior.

3. Spasmolytic activity

The spasmolytic activity was studied on a rat's isolated duodenum maintained in a survival medium of an aerated Tyrode solution heated to 38° C. according to the technique of Magnus (Magnus R.-Archivs ges. Physiol., 1905, 180, 1–71).

The contracting agent used was barium chloride, the reference antogonist agent being papaverine hydrochloride (R). The average activity of the compounds of formula I (X) in comparison with that of the reference agent was expressed by calculating the ratio of the 50 efficient doses (ED 50) determined graphically on logarithmic paper:

$$\frac{ED\ 50\ (R)}{ED\ 50\ (X)}$$

For example: a substance having a relative activity expressed by the FIG. 2 presents an activity equal to twice that of papaverine hydrochloride.

The results obtained, given in table V, show that the compounds of the invention have an interesting spasmolytic activity.

TABLE V

| No. of compound tested | Spasmolytic activity ED 50 (X) (g/ml) | Spasmolytic activity ED 50 (R) (g/ml) | $\frac{ED\ 50\ (R)}{ED\ 50\ (X)}$ |
|---|---|---|---|
| 3 | $1.2 \times 10^{-6}$ | $2.5 \times 10^{-6}$ | 2.08 |
| 9 | $0.5 \times 10^{-6}$ | $4.05 \times 10^{-6}$ | 8.10 |
| 10 | $3.8 \times 10^{-6}$ | $4 \times 10^{-6}$ | 1.05 |
| 11 | $1.05 \times 10^{-6}$ | $6.5 \times 10^{-6}$ | 6.2 |
| 12 | $1.35 \times 10^{-6}$ | $6.5 \times 10^{-6}$ | 4.8 |
| 13 | $2.25 \times 10^{-6}$ | $3.5 \times 10^{-6}$ | 1.55 |
| 15 | $3 \times 10^{-6}$ | $4.75 \times 10^{-6}$ | 1.6 |
| 16 | $1.5 \times 10^{-6}$ | $4 \times 10^{-6}$ | 2.7 |

TABLE IV

| No. of compound tested | D.P.A. a (X) (%) | D.P.A. a (R) (%) | D.P.A. $\frac{a(X)}{a(R)}$ | D.P.A. or ADRENALINE $\frac{C(X)}{LD\ 50\ (X)} / \frac{C(R)}{LD\ 50\ (R)}$ | ADRENALINE a (X) (%) | ADRENALINE a (R) (%) | ADRENALINE $\frac{a(X)}{a(R)}$ | COLLAGENE a (X) (%) | COLLAGENE a (R) (%) | COLLAGENE $\frac{a(X)}{a(R)}$ | COLLAGENE $\frac{C(X)}{LD\ 50\ (X)} / \frac{C(R)}{LD\ 50\ (R)}$ |
|---|---|---|---|---|---|---|---|---|---|---|---|
| 1 | — | — | — | $8.9 \times 10^{-2}$ | 9 | 91 | $1 \times 10^{-1}$ | 12 | 36 | $3.3 \times 10^{-1}$ | $1.8 \times 10^{-1}$ |
| 2 | — | — | — | $7.2 \times 10^{-2}$ | 15 | 91 | $1.65 \times 10^{-1}$ | 12 | 36 | $3.3 \times 10^{-1}$ | $1.4 \times 10^{-1}$ |
| 3 | 15 | 87 | $1.7 \times 10^{-1}$ | — | — | — | — | 13 | 67 | $1.95 \times 10^{-1}$ | — |
| 4 | — | — | — | $1.1 \times 10^{-1}$ | 78 | 78 | 1 | 39 | 88 | $4.5 \times 10^{-1}$ | $2.3 \times 10^{-1}$ |
| 5 | 8 | 53 | $1.5 \times 10^{-1}$ | $8.3 \times 10^{-2}$ | 84 | 78 | 1.1 | 12 | 88 | $1.4 \times 10^{-1}$ | $1.7 \times 10^{-1}$ |
| 6 | 15 | 87 | $1.7 \times 10^{-1}$ | — | — | — | — | 32 | 93 | $3.5 \times 10^{-1}$ | — |
| 9 | 15 | 79 | $1.9 \times 10^{-1}$ | $<9 \times 10^{-2}$ | 86 | 86 | 1 | 16 | 51 | $.3 \times 10^{-1}$ | $1.8 \times 10^{-1}$ |
| 11 | 10 | 55 | $1.8 \times 10^{-1}$ | $10^{-1}$ | 51 | 88 | $5.8 \times 10^{-1}$ | 12 | 36 | $3.3 \times 10^{-1}$ | $1.95 \times 10^{-1}$ |
| 12 | 29 | 79 | $3.6 \times 10^{1}$ | $2.15 \times 10^{-1}$ | 80 | 88 | $9.1 \times 10^{-1}$ | 12 | 53 | $2.3 \times 10^{-1}$ | $4.3 \times 10^{-1}$ |
| 13 | 18 | 79 | $2.3 \times 10^{-1}$ | $1.4 \times 10^{-1}$ | 84 | 77 | 1.1 | — | — | — | — |
| 14 | — | — | — | $1.3 \times 10^{-1}$ | 42 | 77 | $5.5 \times 10^{-1}$ | — | — | — | — |
| 15 | 17 | 85 | $2\ 10^{-1}$ | $1.15\ 10^{-1}$ | 82 | 86 | $9.5 \times 10^{-1}$ | — | — | — | — |
| 16 | 47 | 85 | $5.5 \times 10^{-1}$ | $9 \times 10^{-2}$ | — | — | — | 92 | 36 | 2.5 | $1.8 \times 10^{-1}$ |

TABLE V-continued

| No. of compound tested | Spasmolytic activity ED 50 (X) (g/ml) | Spasmolytic activity ED 50 (R) (g/ml) | ED 50 (R) / ED 50 (X) |
|---|---|---|---|
| 17 | $2.15 \times 10^{-6}$ | $7.25 \times 10^{-6}$ | 3.4 |

4. Analgesic and anti-inflammatory activity

The intraperitoneal injection of phenylparaquinone (P.P.Q.) in a mouse causes the appearance of a painful syndrome appearing within 5 minutes of the injection and disappearing after about 30 minutes (SIEGMUND E. A., CADMUS A., LU G., J. Pharmacol. Exp. Therap. 1957, 119, 453). This painful syndrome manifests itself in the animal by a series of characteristic crises, more or less close together and fleeting, during which we can note a twisting or stretching of the body, a hollowing of the sides and a stretching of the hind legs.

It is therefore possible to note the number of crises in a given interval of time.

The preventive administration of analgesic or anti-inflammatory substances prevents the appearance of crises or reduces the frequency thereof.

The reference substance (R) used in the tests was the ester of N-(7-chloro-4 quinolyl) anthranilic acid and 2,3-dihydroxy n.propanol (known under the trademark Galfenine).

It was administered orally with a dose of 25 mg/kg.

The compounds of formula I (X) were administered digestively with a dose of 50 mg/kg.

The interval of time (t) which was chosen to evaluate the analgesic activity was between 10 and 15 minutes which is the period of maximum frequency of the crises. This activity was expressed in the following way:

n: number of crises observed in the control mice;
n': number of crises observed in mice previously treated with the reference substance (R);
n'': number of crises observed in mice having received the substance (X).

The percentage activity of R is equal to $$\frac{(n-n') \times 100}{n} = a(R)$$

The percentage activity of X is equal to $$\frac{(n-n'') \times 100}{n} = a(X)$$

The activity of X in relation to that of R is estimated by the ratio $$\frac{a(X)}{a(R)}$$

For example: a compound X for which $$\frac{a(X)}{a(R)}$$

is 0.5 has an activity equal to half that of the reference product.

Table VI following gives the results observed.

In addition, so as to permit a better appreciation of the compounds of the invention table VI shows the values of the ratio:

$$\frac{\text{Adm. dose }(X)}{\text{LD 50 }(X)}$$

TABLE VI

| No. of compound tested | Analgesic and anti-inflammatory activity | | | Adm. dose (X) / LD 50 (X) |
|---|---|---|---|---|
| | a(X) | a(R) | a(X)/a(R) | |
| 2 | 38 | 75 | $5 \times 10^{-1}$ | $3.3 \times 10^{-2}$ |
| 6 | 55 | 77 | $7 \times 10^{-1}$ | — |
| 9 | 47 | 45 | 1 | $<4.2 \times 10^{-2}$ |
| 11 | 48 | 75 | $6.5 \times 10^{-1}$ | $4.5 \times 10^{-2}$ |
| 12 | 68 | 45 | 1.5 | $10 \times 10^{-2}$ |
| 14 | 39 | 74 | $5.3 \times 10^{-1}$ | $5.9 \times 10^{-2}$ |
| 15 | 51 | 45 | 1.13 | $5.3 \times 10^{-2}$ |
| 16 | 44 | 75 | $5.9 \times 10^{-1}$ | $4.2 \times 10^{-2}$ |
| 17 | 55 | 45 | 1.2 | $5 \times 10^{-2}$ |

This table shows that for a dose administered corresponding to a small fraction of the lethal dose some compounds of formula I have an analgesic and anti-inflammatory activity similar to that of the reference product.

Other compounds have an activity representing approximately 6/10 that of R. This activity must nevertheless be considered interesting since the reference product is a particularly active analgesic.

5. Vaso-dilatatory activity

The vaso-dilatatory activity as regards the smooth musculature of the vessels was demonstrated on the isolated heart of a guinea-pig perfused with a Locke solution maintained at 37° C. after providing the aorta with a cannula.

The coronary flow is recorded, by means of an electronic device fitted with a Fleish totaliser, before and after addition of the substance X under study (concentration: $1 \times 10^{-5}$ g/ml), the reference product (R) being 2,6-bis (diethanolamino) 4,8-dipiperidinopyrimido[5,4-d]pyrimidine (known under the trademark "Dipyridamole") used at a concentration of $1 \times 10^{-5}$ g/ml.

The percentage flow increase P was calculated at the climax of the activity of X or R.

Table VII below gives, as examples, the results observed with some compounds of formula I.

TABLE VII

| Code No. of compound tested | Vaso-dilatatory activity | | P(X)/P(R) |
|---|---|---|---|
| | P (X) | P (R) | |
| 1 | 28 | 43 | $6.5 \times 10^{-1}$ |
| 10 | 60 | 43 | 1.4 |
| 11 | 41 | 53 | $7.75 \times 10^{-1}$ |
| 12 | 33 | 53 | $6.25 \times 10^{-1}$ |
| 15 | 172 | 71 | 2.42 |

This table shows that the vaso-dilatatory activity of the products of the invention ranges from 0.6 to 2.5 times that of the reference product.

These pharmacological results show the interest of the formula I compounds in the treatment of coronary and cardiac insufficiencies, pains of inflammatory and other origins, and spasms.

Formula I compounds can be administered to man and animals orally, rectally or parenterally, particularly associated with the appropriate excipient in each case.

As examples, they may be presented in the form of tablets, pills, gelules, suppositories or injectable solutions.

The daily dosage may, according to the case, range from 50 to 600 mg.

What we claim is:

1. A compound having the formula

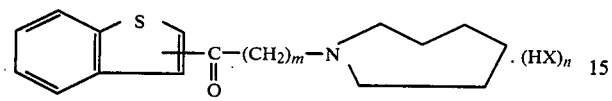

wherein m is 3 or 4,
n is zero or one, and
HX is selected from the group consisting of hydrochloric acid, bromhydric acid, sulfuric acid, phosphoric acid, boric acid, oxalic acid, maleic acid, malic acid, fumaric acid, citric acid, embonic acid, methanesulfonic acid, acetylsalicylic acid, nicotinic acid, parachlorophenoxyacetic acid, parachlorophenoxyisobutyric acid, methyl bromide, methyl iodide, ethyl bromide, butyl bromide and benzyl bromide.

2. A compound as claimed in claim 1, the bromhydric acid addition salt of

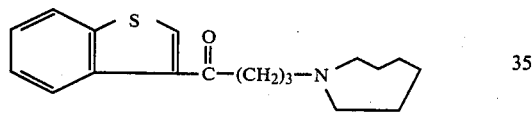

3. A compound as claimed in claim 1, the citric acid addition salt of

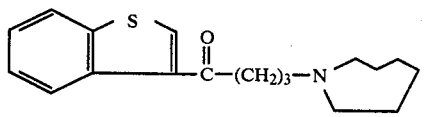

4. A compound having the formula

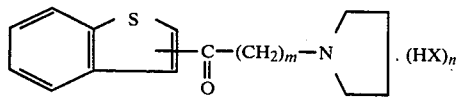

wherein m is 3 or 4,
n is zero or one, and
HX is selected from the group consisting of hydrochloric acid, bromhydrice acid, sulfuric acid, phosphoric acid, boric acid, oxalic acid, maleic acid, malic acid, fumaric acid, citric acid, embonic acid, methanesulfonic acid, acetylsalicylic acid, nicotinic acid, parachlorophenoxyacetic acid, parachlorophenoxyisobutyric acid, methyl bromide, methyl iodide, ethyl bromide, butyl bromide and benzyl bromide.

5. A compound as claimed in claim 4, the bromhydric acid addition salt of

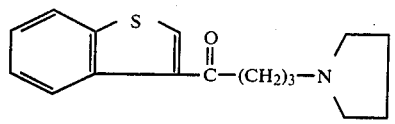

6. A compound having the formula

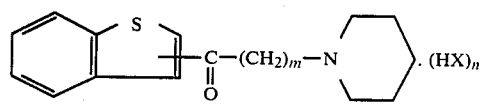

wherein m is 3 or 4,
n is zero or one, and HX is selected from the group consisting of hydrochloric acid, bromhydric acid, sulfuric acid, phosphoric acid, boric acid, oxalic acid, maleic acid, malic acid, fumaric acid, citric acid, embonic acid, methanesulfonic acid, acetylsalicyclic acid, nicotinic acid, parachlorophenoxyacetic acid, parachlorophenoxyisobutyric acid, methyl bromide, methyl iodide, ethyl bromide, butyl bromide and benzyl bromide.

7. A compound as claimed in claim 6, the bromhydric acid addition salt of

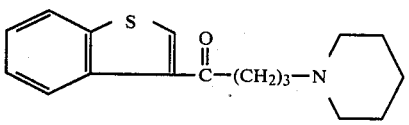

8. A compound having the formula

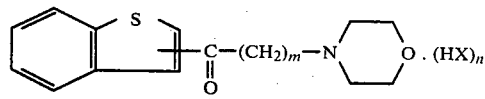

wherein
m is 3 or 4,
n is zero or one, and
HX is selected from the group consisting of hydrochloric acid, bromhydric acid, sulfuric acid, phosphoric acid, boric acid, oxalic acid, maleic acid, malic acid, fumaric acid, citric acid, embonic acid, methanesulfonic acid, acetylsalicylic acid, nicotinic acid, parachlorophenoxyacetic acid, parachlorophenoxyisobutyric acid, methyl bromide, methyl iodide, ethyl bromide, butyl bromide and benzyl bromide.

9. A compound as claimed in claim 8, the bromhydric acid addition salt of

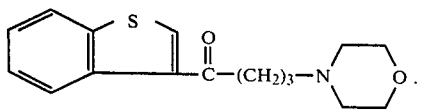

10. A compound as claimed in claim 8, the citric acid addition salt of

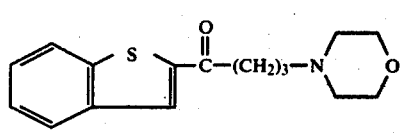
11. A compound as claimed in claim 8, the p-chlorophenoxyisobutyric acid addition salt of
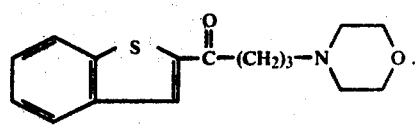
* * * * *